(12) United States Patent
Scales et al.

(10) Patent No.: US 6,220,088 B1
(45) Date of Patent: Apr. 24, 2001

(54) ASSESSMENT OF PATIENT SUPPORT SYSTEMS

(75) Inventors: John Tracey Scales, Pangbourne; Duncan Shirreffs Bain, Middlesex, both of (GB)

(73) Assignee: RAFT Trustees Limited, Middlesex (GB)

( * ) Notice: Subject to any disclaimer, the term of this patent is extended or adjusted under 35 U.S.C. 154(b) by 0 days.

(21) Appl. No.: 08/624,522

(22) PCT Filed: Oct. 11, 1994

(86) PCT No.: PCT/GB94/02218

§ 371 Date: Jun. 6, 1996

§ 102(e) Date: Jun. 6, 1996

(87) PCT Pub. No.: WO95/10762

PCT Pub. Date: Apr. 20, 1995

(30) Foreign Application Priority Data

Oct. 11, 1993 (GB) .................................................. 9320864

(51) Int. Cl.[7] .............................. G01N 1/00; G01N 19/00
(52) U.S. Cl. .............................. 73/172; 73/866.4; 73/774; 73/781
(58) Field of Search ................................... 73/172, 866.4, 73/379.01; 128/774, 781, 779

(56) References Cited

U.S. PATENT DOCUMENTS

| | | | |
|---|---|---|---|
| 3,818,756 | * 6/1974 | Barron et al. | 73/172 |
| 3,822,588 | 7/1974 | Knight et al. | 73/81 |
| 4,140,008 | 2/1979 | Golembeck et al. | 364/468 |
| 4,669,302 | * 6/1987 | Wagner et al. | 73/172 |
| 5,148,706 | 9/1992 | Masuda et al. | 73/172 |
| 5,253,656 | * 10/1993 | Rincoe et al. | 128/782 |

FOREIGN PATENT DOCUMENTS

WO 9510762 of 0000 (WO) .
WO 9520279 of 0000 (WO) .

* cited by examiner

*Primary Examiner*—Hezron Williams
*Assistant Examiner*—Dennis Loo
(74) *Attorney, Agent, or Firm*—Sughrue, Mion, Zinn, Macpeak & Seas, PLLC

(57) ABSTRACT

A method and equipment for assessing the suitability of support surfaces such as mattresses and chairs is disclosed. The method comprises applying a load to each of two such support surfaces with a first indenter having a given profile and a substantially rigid form and measuring the interface pressure, applying the same load to each said surface with a second indenter having substantially the same profile as said first indenter, but having a viscoelastic form and measuring the interface pressure and deriving information as to the characteristics of the supporting surfaces by comparing said measurements. The invention also includes a human phantom for use in testing or comparing support surfaces which comprises a buttocks portion representing the human buttocks and comprising substantially rigid pelvic and femoral parts and a viscoelastic member covering said pelvic and femoral parts, said buttocks portion being pivotably linked to a torso and head portion and the phantom includes means to maintain the torso portion in a plurality of angular positions with respect to the pelvic and femoral parts while making interfacial pressure measurements.

10 Claims, 7 Drawing Sheets

ASSESSMENT OF PATIENT SUPPORT SYSTEMS

BACKGROUND OF THE INVENTION

This invention relates to method and equipment for assessment of patient support systems.

Pressure on the human skin leads to triaxial distortion of the skin and the underlying tissue and comparison and distortion of tissues against the bony skeletons. As a result, the blood vessels which are in these tissues become distorted and this leads to a diminution of the blood supply causing ischaemia with resultant tissue necrosis. This is manifest by the development of pressure sores which, if not carefully treated, do not heal but become chronic and more and more extensive. The problem is particularly prevalent in patients who are elderly or disabled and confined for long periods to bed or to a wheelchair.

Frequently, patients admitted to hospital develop pressure sores during their treatment, and the additional nursing cost of treating pressure sores is considerable.

In one recent study (see A. B. Ward, Prescriber's Journal, 30(6) 1990), it was stated that between 3 and 11% of all patients admitted to hospital develop a pressure sore, and the average duration of treatment for those with significant lesions is 51 days at an estimated cost of £26,000. It has been estimated (see Turner, Wound Management, 1(1), April 1991) that the care of patients suffering from pressure sores is costing the National Health Service as much as £200,000,000 per annum.

A variety of patient support devices and equipment have been developed in an effort to prevent, and/or assist the recovery from, pressure sores. The cost of such equipment varies widely and various claims are made for their effectiveness by the manufacturers and distributors. However, there is no proper basis for assessing the value of these claims or the effectiveness of the equipment, since there are no generally accepted protocols or methods for the evaluation and comparison of patients support systems.

While clinical evaluation has been carried out on behalf of individual manufacturers of equipment and by researchers, the number of patients observed in these tests have been too small for proper statistical evaluation. Another approach has been to directly measure the interface pressure between a support surface and the patient, but such measurements are confounded by experimental and repeatability errors, e.g. because of the difficulty of accurately placing a pressure transducer at precisely the same point when testing two patients support surfaces with a given patient. Another difficulty is that measurements can vary as a result of changes in temperature and moisture levels. Further, the use of patients and volunteers makes comparison of various workers findings virtually impossible since the viscoelastic properties of patients and volunteers' tissues of various ages is variable. The same groups of patients and volunteers cannot be available at all times world-wide which would be required for accurate comparisons.

SUMMARY OF THE INVENTION

The present invention arises from a different approach to the problem of assessing support surfaces and is based on the recognition that the tissue of the patient's body and the surface on which he is supported are both distorted by the act of making measurements of interfacial pressure.

According to one aspect of the present invention, there is provided a method of comparing the suitability of two surfaces for supporting a person thereon, which comprises applying a load to each of said surfaces, with a first indenter having a given profile and a substantially rigid form, and measuring the resulting interface pressure, applying the same load to each of said surfaces using a second indenter having the same profile as said first indenter, but having a viscoelastic form and measuring the interface pressure and deriving information as to the characteristics of the supporting surfaces by comparing the interfacial pressure measurements.

A large discrepancy in the pressures measured for a given surface using the two indenters, indicates that interfacial pressure was reduced by the deformation of the viscoelastic indenter. This may be assumed to be translated in practice to a high degree of local distortion of the patient's skin, thereby providing unsatisfactory support conditions. On the other hand, a closer conformity in pressure between the two measurements indicates that the deformable indenter has generally maintained its shape during the measurement, thus suggesting that the support system was capable under the conditions of loading of taking up a form approximating to that of the deformable indenter.

Thus, by comparing interfacial pressure measurements for the two indenters over a range of applied loads and conditions, a more reliable picture can be developed of the relative performance of two support surfaces.

At this stage, it is not believed to be essential that the deformable indenter has a degree of deformability which conforms accurately to that of parts of the human body. However, it is believed that the best results will be obtained by attempting to mimic the deformability of parts of the human body, such as the buttocks, which contact a support surface such as a bed or a chair.

Materials exist at the present time which have been designed as tissue prostheses. For example, silicone polymers are used extensively for manufacture of artificial breast prostheses. Such materials can be produced to provide a variety of different degrees of deformability, depending upon the polymerisation mix and polymerisation conditions. One supplier of such materials is Amoena (UK) Limited of Chandlers Ford, Eastleigh, Hampshire, England.

In a more sophisticated development of the concept of the present invention, an anatomical phantom can be constructed which can be provided with interchangeable rigid and viscoelastic parts, which will represent rear profiles of one or more of the head, shoulders, arms, buttocks, legs and heel components of a person. The parts of the phantom may be articulated to mimic at least a part of the movements of a human skeleton so that measurements can be taken of interfacial pressures at points along the contacting surfaces between the phantom and the support structure at different angular positions, both of the support surface (if appropriate) and/or of the phantom. Thus, for example, a bed which is designed to be used in the supine position and in the sitting position can be tested for its suitability for nursing patients with a predilection towards pressure sores, in the two main angular positions of the bed.

While current investigations suggest that the support characteristics of beds and cushions can be determined most readily by the method described above, using both rigid and deformable indenters, particularly but not exclusively in the case of the fully developed human phantom it may be possible to measure the deformation of the critical parts or the pressure applied to them, such as the buttocks, by direct imaging techniques or by incorporating pressure transducers or load sensors within the deformable parts. For example, direct imaging can be achieved by radiographic techniques. One way in which radiographic techniques can be employed is to attach metal (eg lead) foil strips to the surface of the deformable part or within the part and, by using radiography, to record the change on its profile under load as a stereo image.

Another feature of the present invention is that the human phantom can be provided with temperature controlled sweating characteristics. This will enable the heat and water vapour transfer values of the support surface to be measured in a situation which mimics the conditions at the surface in use.

According to a further aspect of the present invention, therefore, there is provided a human phantom comprising mutually articulated parts, having components manufactured from viscoelastic materials.

Preferably, these viscoelastic materials are interchangeable with rigid materials of similar profile. The phantom is conveniently open at the upper side to provide convenient points for supporting and/or articulating the phantom or providing access for at which loads are applied predefined in a repeatable configuration, with respect to any support surface under test. Transducers are located at predefined points on the under side of the phantom so that interfacial pressure measurements can be made at a number of desired points on the surface of the phantom.

Alternatively some or all of the transducers can be located between the "skeleton" of the phantom and the deformable parts. This technique enables the contact point at which pressure is to be measured to be accurately predetermined and it avoids distortions caused by tension or slipping between the surface of the phantom and the material of the support surface. In this embodiment the pressure transducers may be attached to the part of the "skeleton" representing the main bony prominences beneath the deformable part or incorporated or encapsulated within the deformable part. It has been found by the inventors that it is only necessary to measure the contact pressures in a small number of areas on the phantom to give a substantially complete representation of the performance of a support surface in reducing the likely occurance of pressure sores. The primary areas are the heel, sacrum, and ischial tuberosities and it is in one or more of the deformable portions representing these parts of the human body where the major incidence of pressure sores occurs.

The phantom of the present invention will thus provide a repeatable test and analysis tool accurately representing the dynamic response of a relaxed human body in a lying or sitting position. The test and assessment method will be applicable to the testing of beds, chairs and trolleys for domestic, hospital or transport use.

BRIEF DESCRIPTION OF THE DRAWINGS

The following specific description illustrates the operation of the method in accordance with the present invention.

In the accompanying drawings.

For example, the phantom may consist of an articulated half-body shell constructed from glass-reinforced resin, e.g. glass-reinforced polyester resin. The components of the body shell can be moulded to represent the rear profiles of the head, arms, torso, legs and heels. Some of the components, e.g. the buttocks and the heels can have interchangeable rigid and viscoelastic sections, and the dimensions will generally conform to average anthropomorphic data. The articulated joints are designed to allow the phantom to be used in reclining, semi-reclining and sitting positions and there is provision for determining the angles of the joints and for monitoring any changes that may occur during tests. Means can also be provided for establishing desired angles in the X and Y planes of the phantom.

Generally, the phantom will have a body weight of the order of 60 to 70 kgs, but varying loadings may be applied. This may be achieved, for example, by mounting the phantom beneath a carriage in such a way that the phantom has unrestricted movement in the X and Y planes but none in the Z plane. Such a carriage can provide a complete test rig enabling the loads applied at various points along the phantom to be measured and the positions

DETAILED DESCRIPTION OF THE PREFERRED EMBODIMENT

Figure 1:
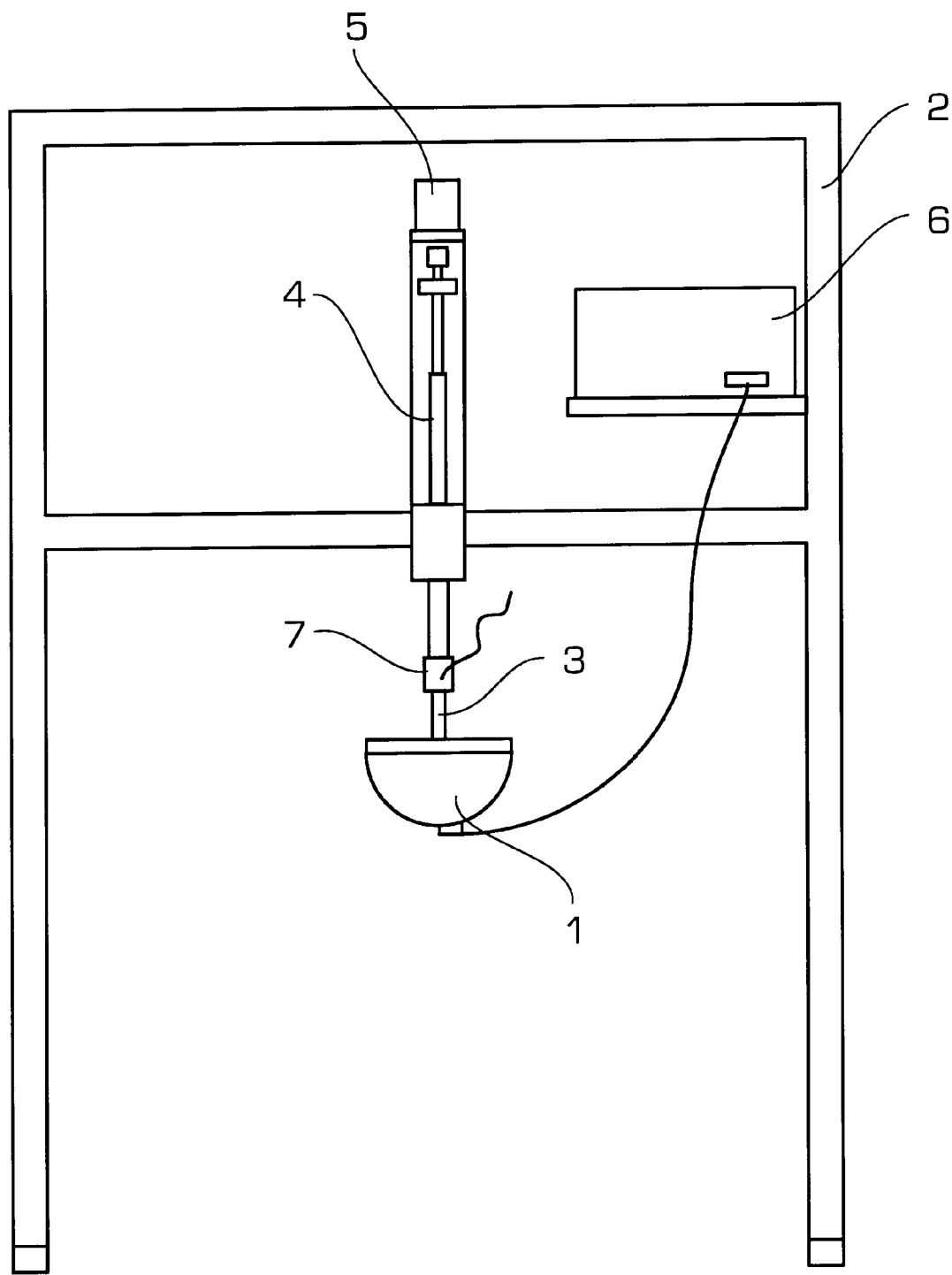
FIG. 1 is a photograph of a test rig showing a hemispherical indenter supported on a motorised screw device.

Referring to FIG. 1, this shows a typical test rig for measuring interfacial pressures. The dome-shaped indenter is applied to the support surface and interfacial pressures are measured using a miniaturised transducer placed at a known point of contact between the indenter and the support surface. Pressures are measured at different applied loads.

As can be seen in FIG. 1, the indenter 1 in the form of a 7 inch diameter rigid plastic dome is supported from a gantry 2 on a spindle 3, which can be moved along an axis towards and away from a support surface to be tested (not shown), placed beneath the gantry. Spindle 3 is attached to a threaded rod 4 which is driven by an electric motor 5. The end of the spindle is connected to a load cell 7 and means for applying varying load to the spindle and hence to the support surface to be tested. Attached to the outer surface of the indenter, (e.g. with adhesive) in selected positions are one or more pressure transducers which are connected to the pressure monitor 6. The pressure transducers are of the kind comprising a pouch of plastic material which can be inflated to a series of known pressures. By measuring the back pressures generated when the pouch is pressed between two surfaces the interfacial pressures may be calculated using the monitor 6. Suitable equipment is manufactured by Oxford Instruments Ltd under the trade name 'Oxford Pressure Monitor'.

Figure 2:
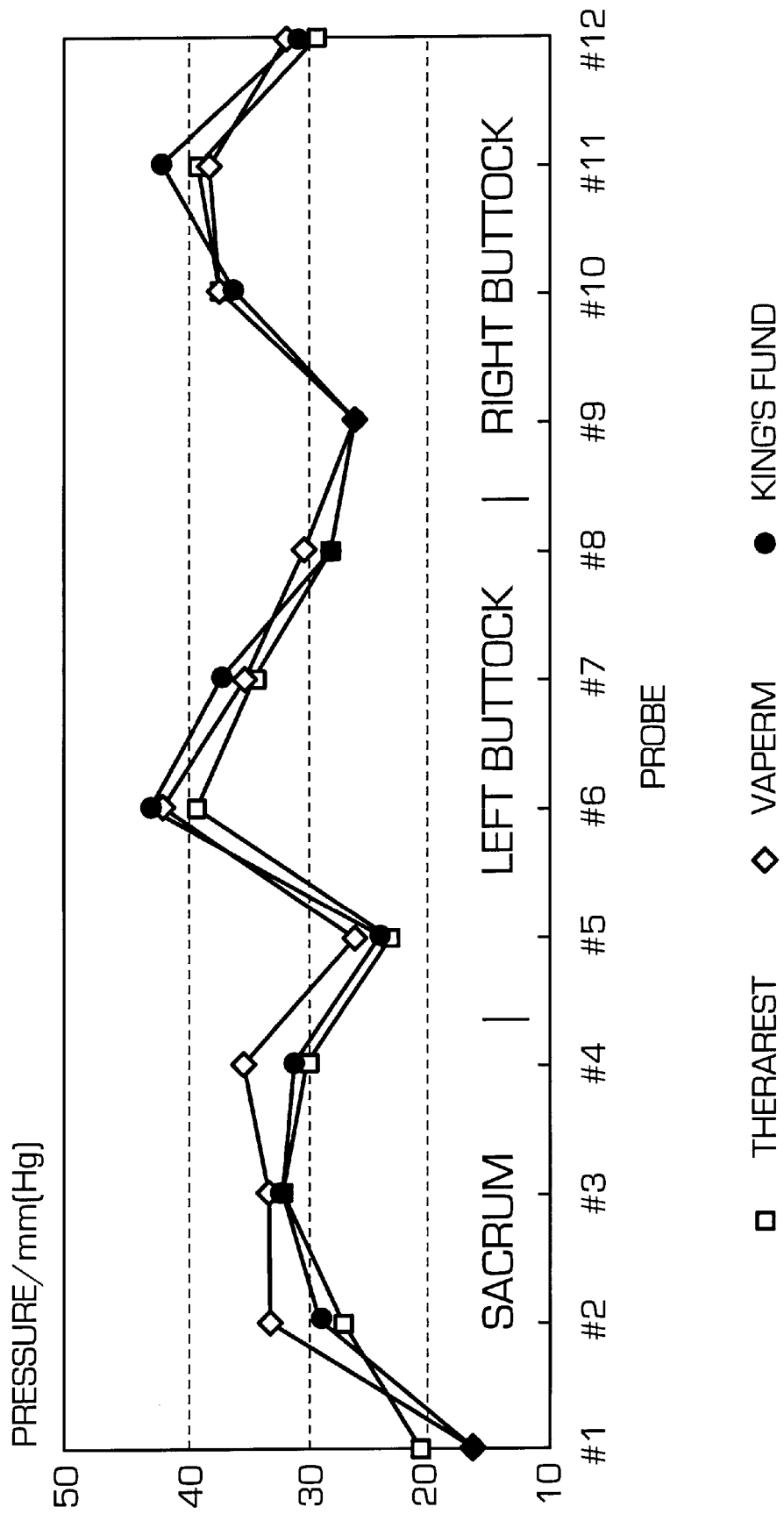
FIG. 2 is a graph showing interfacial pressures of three support systems tested using a human subject.

Referring to FIG. 2, this shows a comparison made of three widely used hospital mattresses by direct measurements taken on a human subject. These measurements were made of interfacial pressures at predefined points on the patient's body and care was taken to place the patient in the same relative position on each mattress and to attach the miniaturised transducers at the same points on the patient's body. The predefined points are achieved by using a polymethylmethacrylate moulding of the patient's or volunteer's buttocks which has been drilled at the appropriate places and when fitted on the body, allows the skin to be marked. Using this method, an accurate as possible location of pressure transducers can be achieved. Even with this method a 20% difference in pressure measurements can result. As can be seem from the graph, there is apparently no significant difference between the performances of the three mattresses when tested by this technique.

Figure 3:
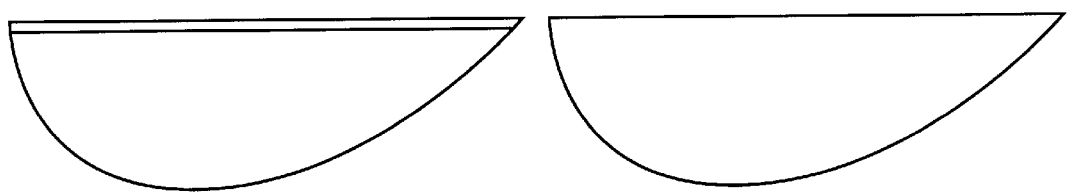
FIG. 3 is a photograph of rigid and viscoelastic indenters, which can be mounted on the equipment shown in FIG. 1.
Figure 4:
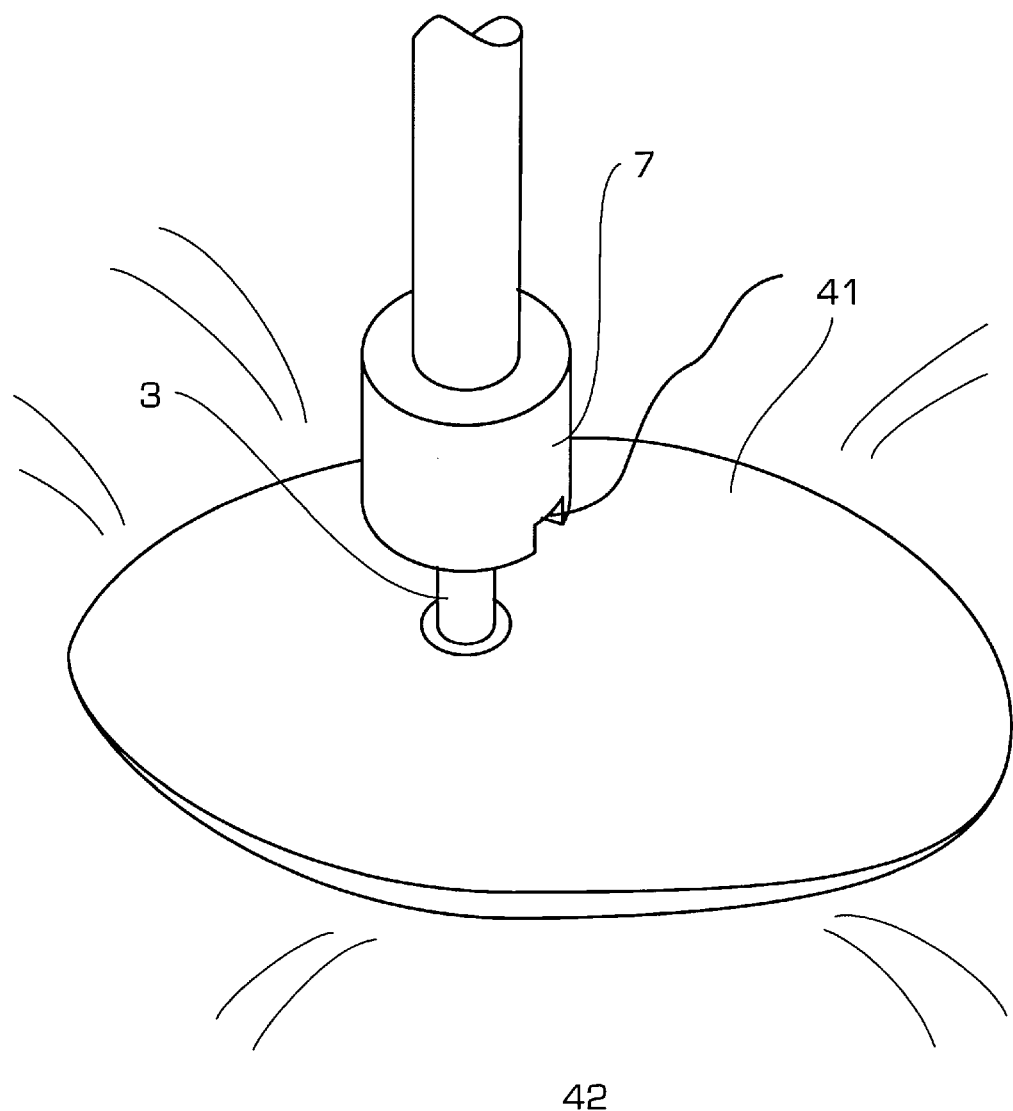
FIG. 4 illustrates the application of a force to one of the indenters shown in FIG. 3.
Figure 5:
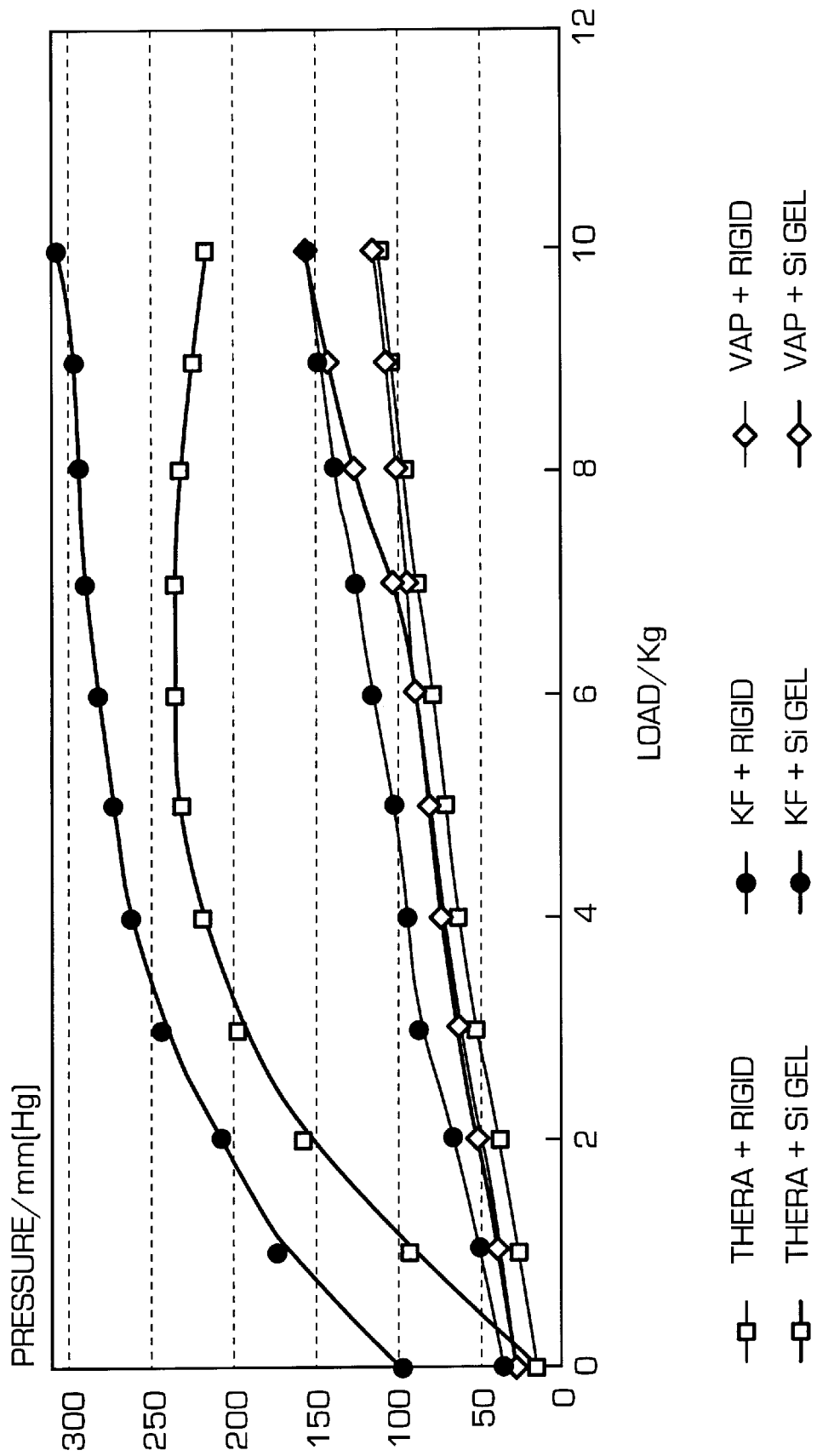
FIG. 5 shows a comparison of interfacial pressures using hard and soft indenters of three support surfaces.

In a further series of tests on the same three mattresses, the test rig shown in FIG. 1 was used. However, the 7" dome shown in FIG. 1 was replaced with a rigid, polyacrylic breast-like shape 41 and subsequently with a deformable indenter having the same profile but manufactured using a viscoelastic silicon polymer as depicted in FIG. 3. Measurements were repeated using the test rig in FIG. 1 of interfacial pressures at corresponding points with the soft and hard indenters for the three mattresses at a number of different loadings, and the results are shown in FIG. 5. FIG. 4 shows the application of the indenter 41 to a mattress support surface 42 under test. As can be seen the indenter 41 is supported on the spindle 3 and varying loads are applied through the load cell 7. As can be seen from the code at the foot of the graph in FIG. 5, the thin lines represent measurements taken with each of the mattresses using the deformable indenter, while the thick lines represent measurements taken with the rigid indenter.

Referring to FIG. 5, it can be readily seen in accordance with the assessment method of the present invention that the measurements of interfacial pressure are not the same when using the hard and soft indenter. For a particular mattress, a marked difference between the pressures measured with the soft and hard indenters would indicate an inability of the mattress to conform to the body under load, and would suggest a mattress which is likely to cause pressure sores.

Pressures can also be measured using a transducer located between the flexible indenter and the support stem or spindle 3 and in this case it is not necessary to make comparative measurements using a rigid indenter.

As will be seen from FIG. 5, the Vaperm mattress performed very satisfactorily having curves which are also generally coincident in this test. This supports the general clinical perception that Vaperm mattresses perform very satisfactorily in hospital use, so far as pressure sore incidence is concerned.

The method described above enables the deformation characteristics for a given support system to be described as the ratio of the pressures obtained using interchangeable standard rigid and deformable units in the sacral and buttock area and in the heel of the human body phantom in which the body loading can be varied for example from 60–90 Kg. It will be appreciated that the method described enables a variety of support surfaces, including mattresses, beds, chairs and cushions to be compared and assessed objectively. In particular, support surfaces which are likely to cause pressure sore development can be accurately identified.

Figure 6:
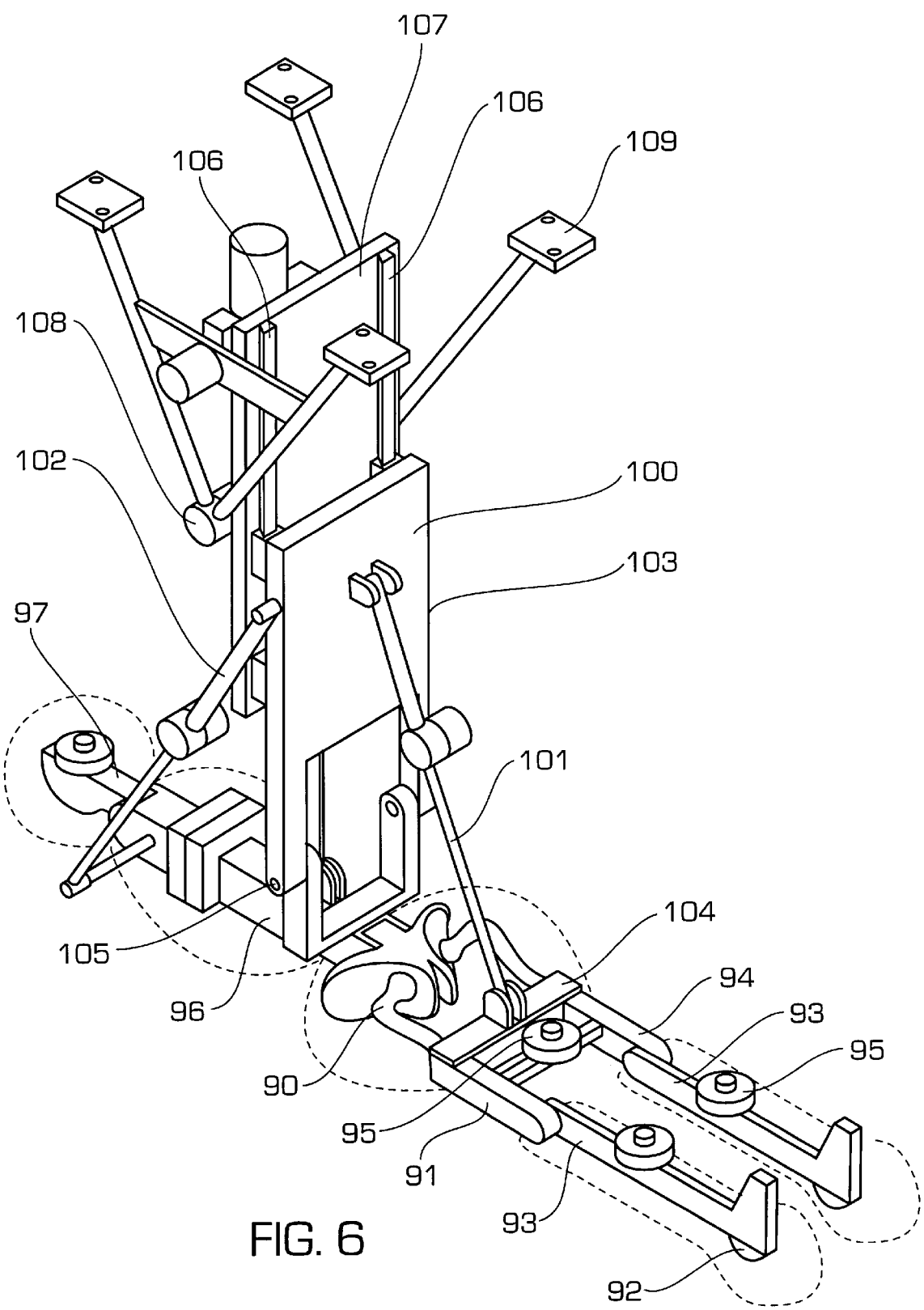
FIG. 6 shows a perspective schematic view of the frame work and supporting structure of a human phantom in accordance with the invention.
Figure 7:
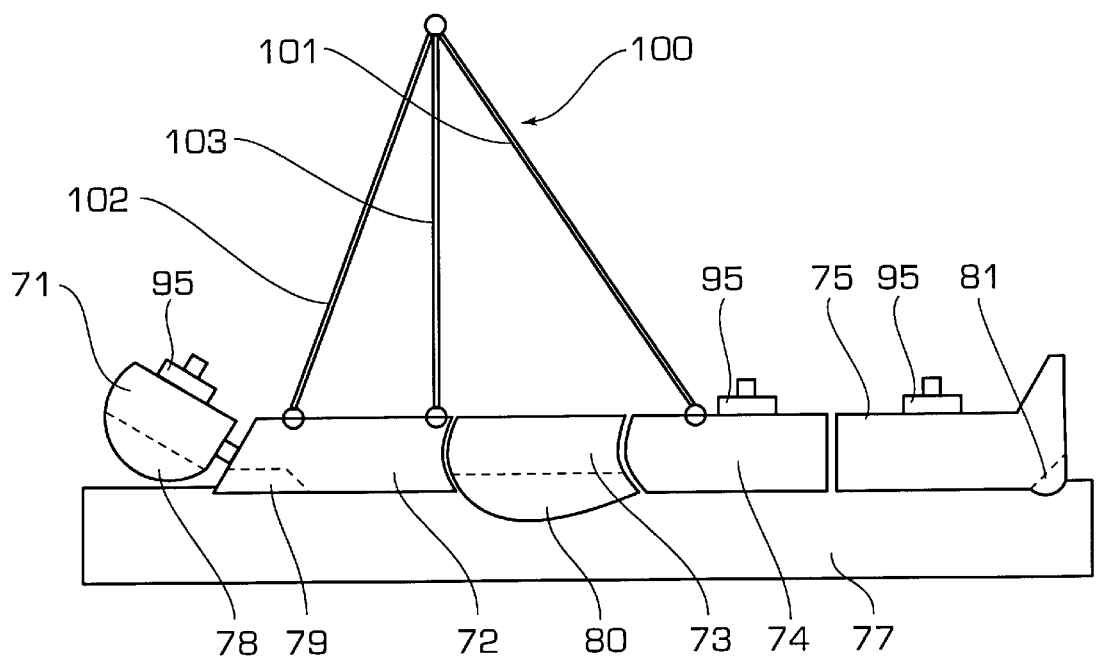
FIG. 7 shows a schematic side elevation of the phantom shown in FIG. 6. instrumentation, connection to heating and/or artificial 'sweating' means so that different parts of the phantom can be loaded to various levels.

Referring to FIGS. 6 and 7, these show schematically one embodiment of the human phantom. For ease of understanding, FIG. 6 shows the framework and support frame with the external parts ghosted. In FIG. 7, the external shell is shown with a part of the support frame shown schematically.

The phantom essentially consists of a series of shell parts representing human body members. As shown in FIG. 7, these comprise a head 71, a torso 72, buttocks 73, thigh 74 and leg and foot 75. These parts are conveniently manufactured as hollow shells, e.g. from glass-fibre reinforced resin. The shells are preferably open above to allow access for an attitude frame 100, instrumentation and adding known loads.

As best seen in FIG. 7, the phantom is placed on a support surface to be tested, e.g. a mattress 77, the attitude frame 100 enabling the phantom to be placed in a precisely, predetermined and repeatable position and attitude on the support surface. Some or all of the members 71–75 can be replaceable partly or wholly with members of the same shape but manufactured from viscoelastic materials or partially therefrom. For example, it may be preferable to replace the members with composite members of the same shape having portions 78, 79, 80 and/or 81 which are made from viscoelastic material, the remainder of the member being manufactured from a stiff, substantially rigid material, such as g.r.p. or metal. It will be appreciated that the portions 78, 79, 80 and 81 represent those parts of the human body which are most prone to the development of pressure sores. In order to represent more faithfully the physical/mechanical characteristics of the human body, the viscoelastic parts may incorporate internal rigid parts representing bones. This is illustrated in FIG. 6, in which it can be seen that the 'skeletal' frame includes a pelvic/femoral part 90 and heel parts 92.

The 'skeletal' frame of the phantom and the attitude frame is shown in FIG. 6. The skeletal frame includes the pelvic/femoral part 90 which is connected to a thigh part 91 and to leg parts 93. Preferably, the parts 91 and 93 are connected by pivotable links 94 which can be locked in a fixed position, e.g. by magnetically operated locks. Parts 91 and 93 are provided with studs on which weights 95 can be threaded so that different parts of the skeletal frame can loaded with known loads. A torso part 96 is connected to the pelvic part 90, also by a pivotable link, which again may be lockable at a number of desired angles with respect to the pelvic part. Torso part 96 is connected to the head 97 by a pivotable and lockable link and is also provided with means for applying known loads 95 to the head part.

The skeletal frame depends from an attitude frame 100, enabling the phantom to be lowered and placed in a desired, repeatable position and in a desired, repeatable attitude (e.g. supine or sitting) on a support surface to be tested. The skeletal frame is connected by struts 101 and 102 to a carriage 103. Strut 101 is attached to the thigh portion 91 by a cross member 104 to prevent the skeletal frame twisting. Both struts 101,102 may be of adjustable lengths in order to vary the relative inclination of parts of the skeletal frame.

As can be seen, the skeletal frame is pivotably mounted at 105 on the carriage 103. Carriage 103 is mounted for sliding movement on a pair of tracks 106, the tracks being carried on a plate 107. Plate 107 is mounted on gimbels 108 which can be attached to a solid, overhead structure (not shown) by feet 109. It will be appreciated that the carriage 103 can be raised and lowered on the tracks 106, e.g. by a cable attached to the carriage (not shown), passing over a pulley on the overhead structure and driven by a winch or linear actuator.

At the same time, the attitude of the skeletal frame can be adjusted by lengthening or shortening the struts 101,102 and/or by pivoting the plate 107 with respect to the gimbels 108, e.g. using a linear actuator. In this way, a support structure can be placed beneath the phantom in a predetermined position and the interfacial pressures developed between the phantom and the support surface measured under a variety of known loads and at a number of preselected angular attitudes of the phantom. The pressures may be measured using pressure transducers attached to the outside of the body members 71~75, particular to the parts 78, 79, 80 and 81. The pressure transducers may be of the kind described above in relation to FIG. 1. It will be appreciated that once the attitude of the phantom has been selected and established, the cable or actuator holding the carriage 103 on the tracks 106 will be allowed to go free so that the whole mass of the phantom will rest on the support surface.

Instead of locating the pressure transducers on the outside of the parts 78, 79, 80 or 81 they may be incorporated within one or more of these deformable parts. Preferably the pressure transducers or load sensors are located on the hard, skeletal parts on these components and the deformable portions 78, 79, 80 or 81 then fitted over them. In practice it may be sufficient to fit load sensors/pressure transducers in the portion 80 on the bony protuberances 90 and 95. With this embodiment it may not be necessary to provide rigid parts corresponding with the deformable parts 78, 79, 80 and 81. Instead sufficient information may be obtainable concerning the behaviour of the support surface under test by direct measurement of pressures or loads at the bony prominences or within the deformable parts.

What is claimed is:

1. A method of comparing the suitability of two surfaces for supporting a person thereon which comprises applying to each of said surfaces a human phantom having substantially rigid skeletal parts and an external profile presenting the human form, said profile being constructed at least partially from one or more viscoelastic or deformable members in which at least one pressure transducer or load sensor is incorporated and comparing the pressures or loads registered on said transducers when said phantom is applied to each of said surfaces.

2. A method as claimed in claim 1, wherein the transducer or sensor is located on a portion of the skeletal parts which represent the sacrum, ischial tuberosities or heel.

3. A method according to claim 1, wherein said viscoelastic or deformable member is applied to the same position under each load and to the equivalent position on the surface to be compared.

4. A method according to claim 3, wherein said member is mounted on a carriage above the support surface, said carriage including means for bringing the member into contact with the surface along a known axis.

5. A method according to claim 1, wherein the support surface is a bed, chair, mattress or cushion.

6. A method as claimed in claim 3, wherein the member is a part or whole human phantom.

7. A part or whole human phantom for use in testing or comparing support surfaces which comprises a buttocks portion representing the human buttocks and comprising substantially rigid pelvic and femoral parts and a viscoelastic or deformable member covering said pelvic and femoral parts.

8. A phantom as claimed in claim 7, wherein said member is detachably fitted to said pelvic and femoral parts.

9. A phantom as claimed in claim 7, wherein one or more pressure transducers or load sensors are incorporated in sid member.

10. A phantom as claimed in claim 7, wherein said buttocks portion is pivotably linked to a torso and head portion and the phantom includes means to maintain the torso portion in a plurality of angular positions with respect to the pelvic and femoral parts while making interfacial pressure measurements between the phantom and a support surface.

* * * * *